United States Patent
Bess et al.

(10) Patent No.: US 7,067,116 B1
(45) Date of Patent: *Jun. 27, 2006

(54) FAST DISSOLVING ORALLY CONSUMABLE SOLID FILM CONTAINING A TASTE MASKING AGENT AND PHARMACEUTICALLY ACTIVE AGENT AT WEIGHT RATIO OF 1:3 TO 3:1

(75) Inventors: William S. Bess, Edison, NJ (US); Neema Kulkarni, Randolph, NJ (US); Suhas H. Ambike, West Hill (CA); Michael P. Ramsay, Ajax (CA)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/535,005

(22) Filed: Mar. 23, 2000

(51) Int. Cl.
- *A61K 9/14* (2006.01)
- *A61K 31/74* (2006.01)
- *A61K 31/785* (2006.01)

(52) U.S. Cl. .............. 424/78.1; 424/78.11; 424/78.12; 424/483; 424/23

(58) Field of Classification Search .............. 514/23, 514/54, 289, 850; 424/9, 78.1, 78.11, 78.12, 424/483

See application file for complete search history.

(56) References Cited

U.S. PATENT DOCUMENTS

| | | | |
|---|---|---|---|
| 3,444,858 A | 5/1969 | Russell | |
| 4,136,145 A | 1/1979 | Fuchs et al. | |
| 4,197,289 A | 4/1980 | Sturzenegger et al. | |
| 4,221,778 A | 9/1980 | Raghunathan | |
| 4,562,020 A | 12/1985 | Hijiya et al. | |
| 4,623,394 A | 11/1986 | Nakamura et al. | |
| 4,713,243 A * | 12/1987 | Schiraldi et al. ............ | 424/676 |
| 4,762,709 A | 8/1988 | Sheumaker | |
| 4,788,055 A | 11/1988 | Fischer et al. | |
| 4,820,506 A | 4/1989 | Kleinberg et al. | |
| 4,925,670 A | 5/1990 | Schmidt | |
| 4,927,636 A | 5/1990 | Hijiya et al. | |
| 4,996,047 A | 2/1991 | Kelleher et al. | |
| 5,023,082 A | 6/1991 | Friedman et al. | |
| 5,047,244 A | 9/1991 | Sanvordeker et al. | |
| 5,354,551 A | 10/1994 | Schmidt | |
| 5,411,945 A | 5/1995 | Ozaki et al. | |
| 5,456,745 A | 10/1995 | Roreger et al. | |
| 5,518,902 A | 5/1996 | Ozaki et al. | |
| 5,529,783 A | 6/1996 | Burke et al. | |
| 5,629,003 A | 5/1997 | Horstmann et al. | |
| 5,700,478 A | 12/1997 | Biegajski et al. | |
| 5,948,430 A | 9/1999 | Zerbe et al. | |
| 5,980,882 A | 11/1999 | Eichman | |
| 6,001,392 A | 12/1999 | Wen et al. | |
| 6,552,024 B1 | 4/2003 | Chen et al. | |
| 6,596,298 B1 * | 7/2003 | Leung et al. ............... | 424/435 |
| 2003/0008008 A1 | 1/2003 | Leung et al. | |
| 2003/0206942 A1 | 11/2003 | Kulkarni et al. | |
| 2003/0211136 A1 | 11/2003 | Kulkarni et al. | |
| 2004/0136922 A1 | 7/2004 | Leung et al. | |

FOREIGN PATENT DOCUMENTS

| | | |
|---|---|---|
| CA | 1313620 | 2/1993 |
| CA | 2234282 | 4/1998 |
| EP | 0225615 | 6/1987 |
| EP | 0 256 611 A1 | 2/1988 |
| EP | 0438147 | 7/1991 |
| GB | 2055575 | 3/1981 |
| JP | 63059855 | 3/1988 |
| JP | 63250318 | 10/1988 |
| JP | 63250319 | 10/1988 |
| JP | 63280014 | 11/1988 |
| JP | 63296655 | 12/1988 |
| JP | 63310817 | 12/1988 |
| JP | 63310818 | 12/1988 |
| JP | 5001198 | 1/1993 |
| JP | 41602 | 6/1993 |
| JP | 5236885 | 9/1993 |
| JP | 10179045 | 12/1996 |
| JP | 2642354 | 5/1997 |
| JP | 9124512 | 5/1997 |
| WO | WO-98/11867 A1 | 3/1998 |
| WO | WO-98/20862 A1 | 5/1998 |
| WO | WO9826763 | 6/1998 |
| WO | WO9826780 | 6/1998 |
| WO | WO9855079 | 12/1998 |
| WO | WO 9917753 | 4/1999 |
| WO | 0042992 | 7/2000 |

OTHER PUBLICATIONS

Shih, Frederick F., "Edible Films from Rice Protein Concentrate and Pullulan," from Cereal Chemistry, vol. 73, No. 3, 1996, pp. 406-409.

(Continued)

*Primary Examiner*—Elli Peselev
(74) *Attorney, Agent, or Firm*—Barry H. Jacobsen; Evan J. Federman

(57) ABSTRACT

Physiologically acceptable films, including edible films, are disclosed. The films include a water soluble film-forming polymer, such as pullulan, and a taste masked pharmaceutically active agent, such as dextromethorphan. The taste masking agent is preferably a sulfonated polymer ion exchange resin comprising polystyrene cross-linked with divinylbenzene, such as AMBERLITE. Methods for producing the films are also disclosed.

33 Claims, No Drawings

OTHER PUBLICATIONS

Krochta, John M. and De Mulder-Johnston, Catherine, "Edible and Biodegradable Polymer Films: Challenges and Opportunities," from Food Technology, vol. 51, No. 2, Feb. 1997, pp. 60-74.

Patent Abstracts of Japan for patent document JP-62-135417, Publication Date: Jun. 18, 1987.

Patent Abstracts of Japan for patent document JP-02-059513, Publication Date: Feb. 28, 1990, and XP-002129504, an English translation of Japanese Patent No. 41602-1993.

* cited by examiner

FAST DISSOLVING ORALLY CONSUMABLE SOLID FILM CONTAINING A TASTE MASKING AGENT AND PHARMACEUTICALLY ACTIVE AGENT AT WEIGHT RATIO OF 1:3 TO 3:1

FIELD OF THE INVENTION

This invention relates to fast dissolving orally consumable films containing an agent to mask the taste of a pharmaceutically active agent therein, and more specifically to such films containing an ion exchange resin as the taste masking agent.

BACKGROUND OF THE INVENTION

It has been known to administer pharmaceutically active agents in an edible film vehicle.

For example, WO 99/17753 discloses rapidly dissolving films for delivery of drugs to be adsorbed in the digestive tract.

WO 98/26780 discloses a flat, foil, paper or wafer type presentation for the application and release of active substances in the buccal cavity. The specific active ingredient disclosed in WO 98/26780 is buprenorphine.

WO 98/20862 discloses a film for use in the oral cavity that can contain a cosmetic or pharmaceutical active substance.

WO 98/26763 discloses a flat, foil, paper or wafer like presentation for release of active substances into the buccal cavity. The particular active disclosed is apomorphine.

U.S. patent application Ser. No. 09/395,104 also discloses the delivery of pharmaceutical agents in a edible film vehicle.

U.S. Pat. No. 5,411,945 to Ozaki et al. discloses a pullulan binder and products produced therewith, including edible films (Example B-2). The products can include a variety of ingredients in addition to pullulan, such as other polysaccharides, antibacterial agents, flavor-imparting agents and pharmaceutically active substances (column 4, lines 5–15).

U.S. Pat. No. 3,784,390 Hijiya et al. discloses pullulan films and their use in coating and packing materials for foods, pharmaceuticals and other oxygen sensitive materials. All of the examples in this patent teach mixing pullulan in hot water.

It has also been known to combine ion exchange resins with pharmaceutically active agents to provide sustained release formulations.

For example, U.S. Pat. No. 6,001,392 to Wen et al. discloses a controlled-release syrup suspension for oral administration containing dextromethorphan adsorbed to a polystyrene sulfonate ion exchange resin. Pharmaceutical films are not disclosed.

U.S. Pat. No. 5,980,882 to Eichman discloses a method for improving the stability of a pharmaceutical composition that contains a drug-resin complex, comprising adding a chelating agent in an amount effective to reduce the rate of degradation of the drug in the drug-resin complex. Although Eichman teaches that complexing a drug with an ion exchange resin can mask the taste of the drug. Pharmaceutical films are not disclosed.

The inventors are not aware of any suggestion in the published art that ion exchange resins can act as taste masking agents in a fast dissolving orally consumable film. Accordingly, an object of this invention is to provide fast dissolving orally consumable films containing an ion exchange resin to mask the taste of a pharmaceutically active agent therein.

All references cited herein are incorporated herein by reference in their entireties.

SUMMARY OF THE INVENTION

The invention provides a consumable film adapted to adhere to and dissolve in a mouth of a consumer, wherein the film comprises at least one water soluble polymer, at least one pharmaceutically active agent and at least one taste masking agent.

Also provided is a method for preparing the consumable film of the invention, comprising:
dissolving water-soluble ingredients in water to provide an aqueous solution;
mixing at least one water soluble film former and at least one stabilizing agent to provide a film-forming mixture;
combining the film-forming mixture and the aqueous solution to provide a hydrated polymer gel;
mixing oils to form an oil mixture;
adding the oil mixture to the hydrated polymer gel and mixing to provide a uniform gel;
casting the uniform gel on a substrate; and
drying the cast gel to provide the film.

DETAILED DESCRIPTION OF PREFERRED EMBODIMENTS

The invention provides a physiologically acceptable film that is particularly well adapted to adhere to and dissolve in a mouth of a consumer to deliver a pharmaceutically active agent. Preferred films according to the invention comprise a pharmaceutically active agent, an ion exchange resin, a film-forming agent, and at least one of the following additional ingredients: water, antimicrobial agents, plasticizing agents, flavoring agents, saliva stimulating agents, cooling agents, surfactants, stabilizing agents, emulsifying agents, thickening agents, binding agents, coloring agents, sweeteners, fragrances, triglycerides, preservatives, polyethylene oxides, propylene glycol, and the like.

The expression "physiologically acceptable" as used herein is intended to encompass compounds, which upon administration to a patient, are adequately tolerated without causing undue negative side effects. The expression encompasses edible compounds.

The expression "pharmaceutically active agents" as used herein is intended to encompass agents other than foods, which promote a structural and/or functional change in and/or on bodies to which they have been administered. These agents are not particularly limited; however, they should be physiologically acceptable and compatible with the film. Suitable pharmaceutically active agents include, but are not limited to:

A. antimicrobial agents, such as triclosan, cetyl pyridium chloride, domiphen bromide, quaternary ammonium salts, zinc compounds, sanguinarine, fluorides, alexidine, octonidine, EDTA, and the like;

B. non-steroidal anti-inflammatory drugs, such as aspirin, acetaminophen, ibuprofen, ketoprofen, diflunisal, fenoprofen calcium, naproxen, tolmetin sodium, indomethacin, and the like;

C. anti-tussives, such as benzonatate, caramiphen edisylate, menthol, dextromethorphan hydrobromide, chlophedianol hydrochloride, and the like;

D. decongestants, such as pseudoephedrine hydrochloride, phenylepherine, phenylpropanolamine, pseudoephedrine sulfate, and the like;

E. anti-histamines, such as brompheniramine maleate, chlorpheniramine maleate, carbinoxamine maleate, clemastine fumarate, dexchlorpheniramine maleate, diphenydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like;

F. expectorants, such as guaifenesin, ipecac, potassium iodide, terpin hydrate, and the like;

G. anti-diarrheals, such a loperamide, and the like;

H. $H_2$-antagonists, such as famotidine, ranitidine, and the like;

I. proton pump inhibitors, such as omeprazole, lansoprazole, and the like;

J. general nonselective CNS depressants, such as aliphatic alcohols, barbiturates and the like;

K. general nonselective CNS stimulants such as caffeine, nicotine, strychnine, picrotoxin, pentylenetetrazol and the like;

L. drugs that selectively modify CNS function, such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like;

M. antiparkinsonism drugs such as levodopa, amantadine and the like;

N. narcotic-analgesics such as morphine, heroin, hydromorphone, metopon, oxymorphone, levorphanol, codeine, hydrocodone, xycodone, nalorphine, naloxone, naltrexone and the like;

O. analgesic-antipyretics such as salycilates, phenylbutazone, indomethacin, phenacetin and the like; and P. psychopharmacological drugs such as chlorpromazine, methotrimeprazine, haloperidol, clozapine, reserpine, imipramine, tranylcypromine, phenelzine, lithium and the like.

The amount of pharmaceutically active agent that can be used in the rapidly dissolving films, according to the present invention, is dependent upon the dose needed to provide an effective amount of the pharmaceutically active agent. Examples of doses for specific pharmaceutically active agents that can be delivered per one strip of rapidly dissolving oral film are reviewed in Table A.

TABLE A

| PHARMACEUTICALLY ACTIVE AGENT | PREFERRED DOSE |
| --- | --- |
| Chlorpheniramine Maleate | 4 mg. |
| Brompheniramine Maleate | 4 mg. |
| Dexchlorpheniramine | 2 mg. |
| Dexbrompheniramine | 2 mg. |
| Triprolidine Hydrochloride | 2.5 mg. |
| Acrivastine | 8 mg. |
| Azatadine Maleate | 1 mg. |
| Loratidine | 10 mg. |
| Phenylephrine Hydrochloride | 10 mg. |
| Dextromethorphan Hydrobromide | 10–30 mg. |
| Ketoprofen | 12.5–25 mg. |
| Sumatriptan Succinate | 35–70 mg. |
| Zolmitriptan | 2.5 mg. |
| Loperamide | 2 mg. |
| Famotidine | 10 mg. |
| Nicotine | 2 mg. |
| Diphenhydramine Hydrochloride | 12.5–25 mg. |
| Pseudoephedrine Hydrochloride | 30 mg. |

Ion exchange resins preferred for use in the films of the invention are water-insoluble and consist of a pharmacologically inert organic or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g., modified cellulose and dextrans). The inorganic matrix can also be, e.g., silica gel modified by the addition of ionic groups. The covalently bound ionic groups may be strongly acidic (e.g., sulfonic acid), weakly acidic (e.g., carboxylic acid), strongly basic (e.g., quaternary ammonium), weakly basic (e.g., primary amine), or a combination of acidic and basic groups. In general, those types of ion exchangers suitable for use in ion exchange chromatography and for such applications as deionization of water are suitable for use in these controlled release drug preparations. Such ion exchangers are described by H. F. Walton in "Principles of Ion Exchange" (pp. 312–343). The ion exchange resins useful in the present invention have exchange capacities below about 6 milliequivalents per gram (meq/g) and preferably below about 5.5 meq/g.

The resin is crosslinked with a crosslinking agent selected from difunctional compounds capable of crosslinking polystyrenes; these are commonly known in the art. Preferably, the crosslinking agent is a divinyl or polyvinyl compound. Most preferably the crosslinking agent is divinylbenzene. The resin is crosslinked to an extent of about 3 to about 20%, preferably about 4 to about 16%, more preferably about 6 to about 10%, and most preferably about 8% by weight based on the total resin. The resin is crosslinked with the crosslinking agent by means well known in the art.

The size of the ion exchange resins should preferably fall within the range of about 20 to about 200 micrometers. Particle sizes substantially below the lower limit are difficult to handle in all steps of the processing. Particle sizes substantially above the upper limit, e.g., commercially available ion exchange resins having a spherical shape and diameters up to about 1000 micrometers, are gritty in liquid dosage forms and have a greater tendency to fracture when subjected to drying-hydrating cycles.

Representative resins useful in this invention include AMBERLITE IRP-69 (obtained from Rohm and Haas) and Dow XYS-40010.00 (obtained from The Dow Chemical Company). Both are sulfonated polymers composed of polystyrene cross-linked with 8% of divinylbenzene, with an ion exchange capacity of about 4.5 to 5.5 meq/g of dry resin (H+-form). Their essential difference is in physical form. AMBERLITE IRP-69 comprises irregularly-shaped particles with a size range of 47 to 149 micrometers, produced by milling the parent, large-sized spheres of AMBERLITE IRP-120. The Dow XYS-40010.00 product comprises spherical particles with a size range of 45 to 150 micrometers. Another useful exchange resin, Dow XYS-40013.00, is a polymer composed of polystyrene cross-linked with 8% of divinylbenzene and functionalized with a quaternary ammonium group; its exchange capacity is normally within the range of approximately 3 to 4 meq/g of dry resin.

The most preferred resin is AMBERLITE IRP-69. However, in less preferred embodiments, the taste masking agent need not be an ion exchange resin. In these embodiments, the taste masking agent can be, e.g., magnesium trisilicate. See, e.g., U.S. Pat. Nos. 4,650,663 and 4,581,232 to Peters et al. Taste can also be masked by polymers, such as EUDRAGIT E (Rohm and Haas), and/or cellulosics, such as ethylcellulose, and the like.

The film-forming agent used in the films according to the present invention can be selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. A preferred film former is pullulan, in amounts ranging from about 0.01 to about 99 wt %, preferably about 30 to about 80 wt %, more preferably from about 45 to about 70 wt % of the film and even more preferably from about 60 to about 65 wt % of the film.

Unless specified otherwise, the term "wt %" as used herein with reference to the final product (i.e., the film, as opposed to the formulation used to create it), denotes the percentage of the total dry weight contributed by the subject ingredient. This theoretical value can differ from the experimental value, because in practice, the film typically retains some of the water and/or ethanol used in preparation.

In embodiments containing relatively high oil content, it is preferable to avoid substantial amounts of humectant in the film (and more preferable to have no humectant in the film), so as to avoid producing an overly moist, self-adhering film. In particular, it is preferred to formulate high oil content films with a plasticizing agent other than glycerin, which is also a humectant, and with a sweetener other than sorbitol, which is a mild humectant.

Saliva stimulating agents can also be added to the films according to the present invention. Useful saliva stimulating agents are those disclosed in U.S. Pat. No. 4,820,506. Saliva stimulating agents include food acids such as citric, lactic, malic, succinic, ascorbic, adipic, fumaric and tartaric acids. Preferred food acids are citric, malic and ascorbic acids. The amount of saliva stimulating agents in the film is from about 0.01 to about 12 wt %, preferably about 1 wt % to about 10 wt %, even more preferably about 2.5 wt % to about 6 wt %.

Preferred plasticizing agents include triacetin in amounts ranging from about 0 to about 20 wt %, preferably about 0 to about 2 wt %. Other suitable plasticizing agents include monoacetin and diacetin.

Preferred cooling agents include monomenthyl succinate, in amounts ranging from about 0.001 to about 2.0 wt %, preferably about 0.2 to about 0.4 wt %. A monomenthyl succinate containing cooling agent is available from Mane, Inc. Other suitable cooling agents include WS3, WS23, Ultracool II and the like.

Preferred surfactants include mono and diglycerides of fatty acids and polyoxyethylene sorbitol esters, such as, Atmos 300 and Polysorbate 80. The surfactant can be added in amounts ranging from about 0.5 to about 15 wt %, preferably about 1 to about 5 wt % of the film. Other suitable surfactants include pluronic acid, sodium lauryl sulfate, and the like.

Preferred stabilizing agents include xanthan gum, locust bean gum and carrageenan, in amounts ranging from about 0 to about 10 wt %, preferably about 0.1 to about 2 wt % of the film. Other suitable stabilizing agents include guar gum and the like.

Preferred emulsifying agents include triethanolamine stearate, quaternary ammonium compounds, acacia, gelatin, lecithin, bentonite, veegum, and the like, in amounts ranging from about 0 to about 5 wt %, preferably about 0.01 to about 0.7 wt % of the film.

Preferred thickening agents include methylcellulose, carboxyl methylcellulose, and the like, in amounts ranging from about 0 to about 20 wt %, preferably about 0.01 to about 5 wt %.

Preferred binding agents include starch, in amounts ranging from about 0 to about 10 wt %, preferably about 0.01 to about 2 wt % of the film.

Suitable sweeteners that can be included are those well known in the art, including both natural and artificial sweeteners. Suitable sweeteners include, e.g.:

A. water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

B. water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

C. dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like;

D. water-soluble sweeteners derived from naturally occurring water-soluble sweeteners, such as a chlorinated derivative of ordinary sugar (sucrose), known, for example, under the product description of sucralose; and E. protein based sweeteners such as thaumatoccous danielli (Thaumatin I and II).

In general, an effective amount of auxiliary sweetener is utilized to provide the level of sweetness desired for a particular composition, and this amount will vary with the sweetener selected. This amount will normally be 0.01% to about 10% by weight of the composition when using an easily extractable sweetener. The water-soluble sweeteners described in category A above, are usually used in amounts of about 0.01 to about 10 wt %, and preferably in amounts of about 2 to about 5 wt %. Some of the sweeteners in category A (e.g., glycyrrhizin) can be used in amounts set forth for categories B–E below due to the sweeteners' known sweetening ability. In contrast, the sweeteners described in categories B–E are generally used in amounts of about 0.01 to about 10 wt %, with about 2 to about 8 wt % being preferred and about 3 to about 6 wt % being most preferred. These amounts may be used to achieve a desired level of sweetness independent from the flavor level achieved from any optional flavor oils used. Of course, sweeteners need not be added to films intended for non-oral administration.

The flavorings that can be used include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth. These flavorings can be used individually or in admixture. Commonly used flavors include mints such as peppermint, artificial vanilla, cinnamon derivatives, and various fruit flavors, whether employed individually or in admixture. Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive, such as those described in Chemicals Used in Food Processing, publication 1274 by the National Academy of Sciences, pages 63–258, may be used. Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, amounts of about 0.1 to about 30 wt % are useable with amounts of about 2 to about 25 wt % being preferred and amounts from about 8 to about 10 wt % are more preferred.

The compositions of this invention can also contain coloring agents or colorants. The coloring agents are used in amounts effective to produce the desired color. The coloring agents useful in the present invention, include pigments such as titanium dioxide, which may be incorporated in amounts of up to about 5 wt %, and preferably less than about 1 wt %. Colorants can also include natural food colors and dyes suitable for food, drug and cosmetic applications. These colorants are known as FD&C dyes and lakes. The materials acceptable for the foregoing spectrum of use are preferably water-soluble, and include FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino) diphenyl-methylene]-[1-N-ethyl-N-p-sulfonium benzyl)-2,5-cyclo-hexadienimine]. A full recitation of all FD&C and D&C dyes and their corresponding chemical structures may be found in the Kirk-Othmer Encyclopedia of Chemical Technology, Volume 5, Pages 857–884, which text is accordingly incorporated herein by reference.

The films can also include a triglyceride. Examples of triglycerides include vegetable oils such as corn oil, sunflower oil, peanut oil, olive oil, canola oil, soybean oil and mixtures thereof. A preferred triglyceride is olive oil. The triglyceride is added to the film in amounts from about 0.1 wt % to about 12 wt %, preferably in a range from about 0.5 wt % to about 9 wt %, of the film.

The films can include a preservative in amounts from about 0.001 wt % to about 5 wt %, preferably from about 0.01 wt % to about 1 wt % of the film. Preferred preservatives include sodium benzoate and potassium sorbate. Other suitable preservatives include, but are not limited to, salts of edetate (also known as salts of ethylenediaminetetraacetic acid, or EDTA, such as disodium EDTA) and parabens (e.g., methyl, ethyl, propyl or butyl-hydroxybenzoates, etc.) or sorbic acid. The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art.

The films can also include a polyethylene oxide compound. The molecular weight of the polyethylene oxide compound ranges from about 50,000 to about 6,000,000. A preferred polyethylene oxide compound is N-10 available from Union Carbide Corporation. The polyethylene oxide compound is added in amounts from about 0.1 wt % to about 5 wt %, preferably from about 0.2 wt % to about 4.0 wt % of the film.

The films can also include propylene glycol. The propylene glycol is added in amounts from about 1 wt % to about 20 wt %, preferably from about 5 wt % to about 15 wt % of the film.

Methods for preparing films according to the invention are capable of encapsulating the oil ingredients within the film-forming matrix and maintaining the integrity of the film, even when the film contains oils in amounts of 10 wt % or more.

In certain methods for preparing films according to the invention, the film-forming ingredients are mixed and hydrated with water separately from the water-soluble ingredients, which are mixed in aqueous solution separately from the organic ingredients and surfactants. In these methods, the final formulation is preferably produced by mixing the film-forming phase with the aqueous phase, then mixing in the organic phase, which includes surfactants, such as Polysorbate 80 and Atmos 300. This mass is mixed until emulsified. In other embodiments, the aqueous and film forming phases are combined into a single phase by dissolving the water soluble ingredients in the water and then adding the gums to hydrate. The organic phase is then added to this single aqueous phase.

The resulting formulation is cast on a suitable substrate and dried to form a film. The film is preferably air-dried or dried under warm air and cut to a desired dimension, packaged and stored. The film can contain from about 0.1% to about 10 wt % moisture, preferably from about 3% to about 8 wt % moisture, even more preferably from about 4 to about 7 wt % moisture.

The film-forming phase can include pullulan and stabilizing agents such as xanthan gum, locust bean gum and carrageenan. These ingredients are mixed and then hydrated in water for about 30 to about 48 hours to form a gel. The water is preferably heated to a temperature of about 25 to about 45° C. to promote hydration. The amount of water is about 40 to 80% of the gel. The resulting hydrated gel is then chilled to a temperature of about 20 to about 30° C. for about 1 to about 48 hours. The water is preferably deionized.

In preferred embodiments, the aqueous phase includes water heated to a temperature of about 60 to 90° C., preferably 70 to 80° C., and ingredients such as the pharmaceutically active agent, ion exchange resin (or other masking agent), coloring agent, preservative and sweetener.

The water is preferably deionized and the amount of water used is about 5 to about 80 wt % of the final gel mixture.

The pharmaceutically active agent is sorbed to the ion exchange resin (or other masking agent) without separating ion exchanged pharmaceutically active agent from unexchanged agent and counter ion salts.

Adsorption of the pharmaceutically active agent onto the ion exchange resin particles to form the pharmaceutically active agent/resin complex is a well known technique as shown in U.S. Pat. Nos. 2,990,332 and 4,221,778. In general, the pharmaceutically active agent is mixed with an aqueous suspension of the resin, and in less preferred embodiments, the complex is then washed and dried. Adsorption of pharmaceutically active agent onto the resin may be detected by measuring a change in the pH of the reaction medium, or by measuring a change in concentration of sodium or pharmaceutically active agent.

Binding of pharmaceutically active agent to resin can be accomplished according to four general reactions. In the case of a basic pharmaceutically active agent, these are: (a) resin (Na-form) plus pharmaceutically active agent (salt form); (b) resin (Na-form) plus pharmaceutically active agent (as free base); (c) resin (H-form) plus pharmaceutically active agent (salt form); and (d) resin (H-form) plus pharmaceutically active agent (as free base). All of these reactions except (d) have cationic byproducts, by competing with the cationic pharmaceutically active agent for binding sites on the resin, reduce the amount of pharmaceutically active agent bound at equilibrium. For basic pharmaceutically active agents, stoichiometric binding of pharmaceutically active agent to resin is accomplished only through reaction (d).

Four analogous binding reactions can be carried out for binding an acidic pharmaceutically active agent to an anion exchange resin. These are: (a) resin (Cl-form) plus pharmaceutically active agent (salt form); (b) resin (Cl-form) plus pharmaceutically active agent (as free acid); (c) resin (OH-form) plus pharmaceutically active agent (salt form); and (d) resin (OH-form) plus pharmaceutically active agent (as free acid). All of these reactions except (d) have ionic byproducts and the anions generated when the reactions occur compete with the anionic pharmaceutically active agent for binding sites on the resin with the result that reduced levels of pharmaceutically active agent are bound at equilibrium. For acidic pharmaceutically active agents, stoichiometric binding of pharmaceutically active agent to resin is accomplished only through reaction (d). The binding may be performed, for example, as a batch or column process, as is known in the art.

In less preferred embodiments, the adsorption complex, including pharmaceutically active agent and resin, is collected and washed with ethanol and/or water to insure removal of any unadsorbed pharmaceutically active agent. The complexes are usually air-dried in trays at room or elevated temperature.

The ratio of the pharmaceutically active agent adsorbate to ion exchange resin adsorbent in the adsorption complex is about 1:3 to about 3:1, preferably about 1:2 to about 2:1, most preferably about 1:1. The only limit to using ratios in excess of 1:3 is an economic and aesthetic one.

The amount of the pharmaceutically active agent adsorbed to the ion exchange resin is in the range from about 25 to about 75% by weight of the pharmaceutically active agent/resin adsorption complex (hereinafter referred to as the "pharmaceutically active agent/resin complex" or "complex"). More preferably, the amount of the pharmaceutically active agent adsorbed to the ion exchange resin is in the range from about 33 to about 77% by weight of the pharmaceutically active agent/resin complex. Most preferably, the amount of the pharmaceutically active agent adsorbed to the ion exchange resin is in the range from about 40 to about 60% by weight of the pharmaceutically active agent/resin complex.

The amount of pharmaceutically active agent/resin complex in the formulation is adjusted to deliver a predetermined dose of the pharmaceutically active agent over a predetermined period of time.

For example, a preferred antitussive film of the invention is administered at one dose every 12 hours to deliver a pharmaceutically effective amount of dextromethorphan over a period of approximately 12 hours to a patient in need of such administration. A typical adult dose of a film of the invention measuring 1"×1.25" (2.54 cm×3.18 cm) weighs about 60 to about 190 mg and contains about 20 to about 130 mg of pharmaceutically active agent/resin complex to deliver about 5 to about 65 mg of pharmaceutically active agent (e.g., dextromethorphan hydrobromide) when the average pharmaceutically active agent:ion exchange resin ratio is about 1:1.

In a particularly preferred embodiment of the invention, pullulan is present in the film in an amount of about 2 to about 6 mg/cm$^2$, dextromethorphan is present in the film in an amount of about 1.4 to about 3 mg/cm$^2$, and sulfonated polymer ion exchange resin is present in said film in an amount of about 1.4 to about 2 mg/cm$^2$.

The antitussive pharmaceutically active agents that are suitable for use in these preparations are acidic, amphoteric or most often basic antitussives. Examples of basic pharmaceutically active agents useful in the present invention include, but are not limited to dextromethorphan, diphenhydramine, caramiphen, carbapentane, ethylmorphine, noscapine and codeine. In addition, the antitussive embodiments of the invention can further comprise additional agents that are therapeutically effective to treat conditions other than coughing. That is, more than one type of pharmaceutically active agent can be included in a film of the invention. For example, in the case of a film containing an antitussive agent, the film can further comprise an antihistamine, sympathomimetic pharmaceutically active agent (nasal decongestant, bronchodilator), analgesic, antiinflammatory, cough suppressant and/or expectorant. Compounds which are antihistamines, sympathomimetic pharmaceutically active agents (nasal decongestant, bronchodilator), analgesic, antiinflammatory, cough suppressants and/or expectorants are well known to those of skill in the art and need not be discussed in detail herein.

In embodiments, a certain percentage of the films disclosed herein will contain non-coated pharmaceutically active agent/resin complexes. The remaining pharmaceutically active agent/resin complexes are further characterized by the presence of a coating. In the preferred embodiment of the present invention, about 20 to about 80% of the pharmaceutically active agent/resin complexes in the sustained-release compositions are coated, most preferably about 40 to about 60% of the pharmaceutically active agent/resin complexes. The coating is a water-permeable, diffusion barrier coating material. The presence of a coating allows one to selectively modify the dissolution profile as desired of a pharmaceutical composition comprising the pharmaceutically active agent/resin complexes of the present invention.

The coating materials can in general be any of a large number of conventional natural or synthetic film-forming materials used singly, in admixture with each other, and in admixture with plasticizers, pigments, etc. with diffusion barrier properties and with no inherent pharmacological or toxic properties. In general, the major components of the coating should be insoluble in water, and permeable to water and pharmaceutically active agent. However, it might be desirable to incorporate a water-soluble substance, such as methyl cellulose, to alter the permeability of the coating, or to incorporate an acid-insoluble, base-soluble substance to act as an enteric coating. The coating materials may be applied as a suspension in an aqueous fluid or as a solution in organic solvents. Suitable examples of such coating materials are described by R. C. Rowe in Materials used in Pharmaceutical Formulation. (A. T. Florence, editor), Blackwell Scientific Publications, Oxford, 1–36(1984), incorporated by reference herein. Preferably the water-permeable diffusion barrier is selected from the group consisting of ethyl cellulose, methyl cellulose and mixtures thereof. Most preferably, the coating material is SURELEASE, manufactured by Colorcon which is water based ethyl cellulose latex, plasticized with dibutyl sebacate or with vegetable oils. Other non-limiting coating materials included within the scope of the present invention are AQUACOAT, manufactured by FMC Corporation of Philadelphia, which is ethylcellulose pseudolatex; solvent based ethylcellulose; shellac; zein; rosin esters; cellulose acetate; EUDRAGITS, manufactured by Rohm and Haas of Philadelphia, which are acrylic resins; silicone elastomers; poly(vinyl chloride) methyl cellulose; and hydroxypropylmethyl cellulose.

Conventional coating solvents and coating procedures (such as fluid bed coating and spray coating) can be employed to coat the particles. Techniques of fluid bed coating are taught, for example, in U.S. Pat. Nos. 3,089,824, 3,117,027, and 3,253,944. The coating is normally applied to the pharmaceutically active agent/resin complex, but alternatively can be applied to the resin before complexing with the pharmaceutically active agent. Non-limiting examples of coating solvents include ethanol, a methylene chloride/acetone mixture, coating emulsions, methyl acetate, tetrahydrofuran, carbonetetrachloride, methyl ethyl ketone, ethylene dichloride, trichloroethylene, hexane, methyl alcohol, isopropyl alcohol, methyl isobutyl ketone, toluene, 2-nitropropane, xylene, isobutyl alcohol, n-butyl acetate.

It is preferred that the coated pharmaceutically active agent/resin complexes are coated in the range from about 40 to about 70% w/w pharmaceutically active agent/resin complex. More preferably, the pharmaceutically active agent/resin complex is coated in the range from about 45 to about 55% w/w pharmaceutically active agent/resin complex. Most preferably, the pharmaceutically active agent/resin complex is coated about 50% w/w pharmaceutically active agent/resin complex. Variation in the amount of coating and/or the use of coated/uncoated complex mixtures can be employed to selectively modify the dissolution profile as desired.

The average particle sizes of the non-hydrated coated and uncoated pharmaceutically active agent/resin complexes is about 60 to about 200 and about 60 to about 250 micrometers, respectively. More preferably, average particle sizes of the coated pharmaceutically active agent/resin complexes is between about 70 and about 190 micrometers, and most preferably about 70 to about 180 micrometers. More preferably, average particle sizes of the uncoated pharmaceutically active agent/resin complexes is between about 55 and about 160 micrometers, and most preferably about 60 to about 150 micrometers. It is desirable that about 85%, preferably about 95%, and most preferably about 98% of the resin particles have sizes within the ranges set forth above. Adjustments within these ranges can be made to accommodate desired aesthetic qualities of the final formulation product. It is more preferable that the resin dextromethorphan complex have particle sizes within these ranges as well.

In embodiments, it is possible to hydrate the film-forming ingredients and combine all of the ingredients without heating. This method comprises dissolving the water-soluble ingredients in water to form an aqueous mixture; mixing the film-forming ingredients in powder form to form a powder mixture; adding the powder mixture to the aqueous mixture to form a hydrated polymer gel; stirring the hydrated polymer at room temperature for about 30 minutes to about 48 hours; mixing the cooling agent, menthol and any other oils to form an oil mixture; adding the oil mixture to the hydrated polymer gel and mixing until uniform; deaerating the film until air bubbles are removed, casting the uniform mixture on a suitable substrate; and drying the cast mixture to form a film. This method hydrates the film-forming ingredients without heating the water, which can reduce energy costs in the manufacturing process and undesirable losses of volatile ingredients to evaporation. Further, mixing the oils in two steps minimizes the amount of flavor lost.

While not wishing to be bound by any theories, it is believed that the film-forming ingredients can be hydrated and mixed without heating due to an ionic effect known as the Donnan equilibrium. Hydrating the film-forming agents in the presence of electrolytes in solution effectively lowers the viscosity of the polymer gel being formed, thus increasing the efficiency of the hydrating process. The water-soluble ingredients of the formulation provide the electrolytes, which are dissolved in the hydration solution prior to addition of the film-forming ingredients. High-shear mixing also accelerates hydration, which delumps the powders, providing greater surface area for water contact. In addition, local heating effects, generated in the shear regions, provide energy for hydration without substantially raising the temperature of the mass.

EXAMPLES

The invention will be illustrated in more detail with reference to the following Examples, but it should be understood that the present invention is not deemed to be limited thereto.

Example 1

The ingredients listed in Table 1 were combined to provide a comparative example of an antitussive film in accordance with the following procedure:

A. The water was heated to 50° C. The potassium sorbate and sweeteners were dissolved in the water with mixing. The titanium dioxide was then added with further mixing to form Preparation A.

B. The film-forming ingredients (e.g., xanthan gum, locust bean gum, carrageenan and pullulan) were mixed in a separate container to form Preparation B.

C. Preparation B was slowly added to Preparation A with rapid mixing, followed by overnight mixing at a reduced rate to provide Preparation C.

D. The glycerin and olive oil were combined in a separate container and then the menthol and monoammonium glycyrrhizinate (MAG) were dissolved therein by heating to 45° C. to form Preparation D.

E. Preparation D was added to Preparation C with thorough mixing and then the flavor agents were added with continued mixing to provide Preparation E.

F. Dextromethorphan coated with ethyl cellulose was then added to Preparation E with mixing. The pH was adjusted as necessary to 6.0 using 10% citric acid solution to provide Preparation F (Examples 1–3 only).

Preparation F was poured on a mold and cast to form a film of a desired thickness at room temperature. The film was dried under warm air and cut to a desired dimension (dictated by, e.g., dosage and mouthfeel) for taste testing. The film was segmented into 1"×1.25" (2.54 cm×3.18 cm) dosage units, each of which had a thickness of 0.009±0.002 in (0.23±0.05 mm) and a weight of 70±3 mg.

A placebo film was also prepared in accordance with the foregoing to facilitate evaluation of, e.g., the taste and appearance of the active film.

TABLE 1

| Material | % w/w in batch | g/batch | % w/w* | mg/dose* | % w/w* active film | % w/w actual batch |
|---|---|---|---|---|---|---|
| Coated Dextromethorphan (55% DM) | | 103.6291 | | 27.3000 | 29.5775 | 9.3899 |
| Xanthan Gum | 0.0600 | 0.6000 | 0.2432 | 0.1581 | 0.1713 | 0.0544 |
| Locust Bean Gum | 0.0700 | 0.7000 | 0.2837 | 0.1844 | 0.1998 | 0.0634 |
| Carrageenan | 0.3000 | 3.0000 | 1.2159 | 0.7903 | 0.8563 | 0.2718 |
| Pullulan | 16.0000 | 160.0000 | 64.8466 | 42.1503 | 45.6666 | 14.4976 |
| Potassium Sorbate | 0.0600 | 0.6000 | 0.2432 | 0.1581 | 0.1713 | 0.0544 |
| Acesulfame Potassium Salt | 0.5000 | 5.0000 | 2.0265 | 1.3172 | 1.4271 | 0.4531 |
| Aspartame NF | 1.4000 | 14.0000 | 5.6741 | 3.6882 | 3.9958 | 1.2685 |
| Purified Water | 75.3264 | 753.2640 | | | | 68.2534 |
| Physcool | 0.1000 | 1.0000 | 0.4053 | 0.2634 | 0.2854 | 0.0906 |
| Menthol | 1.0000 | 10.0000 | 4.0529 | 2.6344 | 2.8542 | 0.9061 |
| Citric Acid | 0.0710 | 0.7100 | 0.2878 | 0.1870 | 0.2026 | 0.0643 |
| Cherry Flavor (Givudan) | 0.1500 | 1.5000 | 0.6079 | 0.3952 | 0.4281 | 0.1359 |
| Peppermint Flavor | 0.5000 | 5.0000 | 2.0265 | 1.3172 | 1.4271 | 0.4531 |
| Mono ammonium glycyrrhizinate (MAG) | 0.0100 | 0.1000 | 0.0405 | 0.0263 | 0.0285 | 0.0091 |
| Polysorbate 80 NF | 0.3500 | 3.5000 | 1.4185 | 0.9220 | 0.9990 | 0.3171 |
| Atmos 300 | 0.3500 | 3.5000 | 1.4185 | 0.9220 | 0.9990 | 0.3171 |
| Glycerine | 3.0000 | 30.0000 | 12.1587 | 7.9032 | 8.5625 | 2.7183 |
| Olive Oil | 0.5000 | 5.0000 | 2.0265 | 1.3172 | 1.4271 | 0.4531 |
| FD&C green #3 | 0.0026 | 0.0260 | 0.0105 | 0.0068 | 0.0074 | 0.0024 |
| Titanium Dioxide | 0.2500 | 2.5000 | 1.0132 | 0.6586 | 0.7135 | 0.2265 |
| Total w/o active | | 0.0000 | 100.0000 | 65.0000 | | |
| Total with active | 100.0000 | 1103.6291 | | 92.3000 | 100.0000 | 100.0000 |

*assuming that all water is evaporated

The active film was gritty and bitter.

Example 2

Comparative films having the ingredients listed in Table 2 were prepared in accordance with the method of Example 1.

TABLE 2

| Material | % w/w in batch | g/batch | % w/w* placebo film | mg/dose* | % w/w* active film | % w/w actual batch |
|---|---|---|---|---|---|---|
| Coated Dextromethorphan (53.5% DM) | | 106.4239 | | 28.0374 | 30.1356 | 9.6187 |
| Xanthan Gum | 0.0600 | 0.6000 | 0.2432 | 0.1581 | 0.1699 | 0.0542 |
| Locust Bean Gum | 0.0700 | 0.7000 | 0.2837 | 0.1844 | 0.1982 | 0.0633 |
| Carrageenan | 0.3000 | 3.0000 | 1.2159 | 0.7904 | 0.8495 | 0.2711 |
| Pullulan | 16.0000 | 160.0000 | 64.8493 | 42.1520 | 45.3065 | 14.4610 |
| Potassium Sorbate | 0.0600 | 0.6000 | 0.2432 | 0.1581 | 0.1699 | 0.0542 |
| Acesulfame Potassium Salt | 0.5000 | 5.0000 | 2.0265 | 1.3173 | 1.4158 | 0.4519 |
| Aspartame NF | 1.4000 | 14.0000 | 5.6743 | 3.6883 | 3.9643 | 1.2653 |
| Purified Water | 75.3274 | 753.2740 | | | | 68.0819 |
| Physcool | 0.1000 | 1.0000 | 0.4053 | 0.2635 | 0.2832 | 0.0904 |
| Menthol | 1.0000 | 10.0000 | 4.0531 | 2.6345 | 2.8317 | 0.9038 |
| Citric Acid (used to adjust pH to 6.0) | 0.0700 | 0.7000 | 0.2837 | 0.1844 | 0.1982 | 0.0633 |
| Cherry Flavor (Givudan) | 0.1500 | 1.5000 | 0.6080 | 0.3952 | 0.4247 | 0.1356 |
| Peppermint Flavor | 0.5000 | 5.0000 | 2.0265 | 1.3173 | 1.4158 | 0.4519 |
| Mono ammonium glycyrrhizinate (MAG) | 0.0100 | 0.1000 | 0.0405 | 0.0263 | 0.0283 | 0.0090 |
| Polysorbate 80 NF | 0.3500 | 3.5000 | 1.4186 | 0.9221 | 0.9911 | 0.3163 |
| Atmos 300 | 0.3500 | 3.5000 | 1.4186 | 0.9221 | 0.9911 | 0.3163 |

TABLE 2-continued

| Material | % w/w in batch | g/batch | % w/w* placebo film | mg/dose* | % w/w* active film | % w/w actual batch |
|---|---|---|---|---|---|---|
| Glycerine | 3.0000 | 30.0000 | 12.1592 | 7.9035 | 8.4950 | 2.7114 |
| Olive Oil | 0.5000 | 5.0000 | 2.0265 | 1.3173 | 1.4158 | 0.4519 |
| FD&C Green #3 | 0.0026 | 0.0260 | 0.0105 | 0.0069 | 0.0074 | 0.0024 |
| Titanium Dioxide | 0.2500 | 2.5000 | 1.0133 | 0.6586 | 0.7079 | 0.2260 |
| Total w/o active |  | 0.0000 | 100.0000 | 65.0000 |  |  |
| Total with active | 100.0000 | 1106.4239 |  | 93.0374 | 100.0000 | 100.0000 |

*assuming that all water is evaporated

The active film was gritty and bitter.

Example 3

Comparative films having the ingredients listed in Table 3 were prepared in accordance with the method of Example 1.

TABLE 3

| Material | % w/w in batch | g/batch | % w/w* placebo film | mg/dose* | % w/w* active film | % w/w actual batch |
|---|---|---|---|---|---|---|
| Coated Dextromethorphan (60% DM) |  | 94.7292 |  | 25.0000 | 27.7778 | 8.6532 |
| Xanthan Gum | 0.0600 | 0.6000 | 0.2436 | 0.1583 | 0.1759 | 0.0548 |
| Locust Bean Gum | 0.0700 | 0.7000 | 0.2842 | 0.1847 | 0.2053 | 0.0639 |
| Carrageenan | 0.3000 | 3.0000 | 1.2180 | 0.7917 | 0.8797 | 0.2740 |
| Pullulan | 16.0000 | 160.0000 | 64.9625 | 42.2256 | 46.9174 | 14.6155 |
| Potassium Sorbate | 0.0600 | 0.6000 | 0.2436 | 0.1583 | 0.1759 | 0.0548 |
| Acesulfame Potassium Salt | 0.5000 | 5.0000 | 2.0301 | 1.3196 | 1.4662 | 0.4567 |
| Aspartame NF | 1.4000 | 14.0000 | 5.6842 | 3.6947 | 4.1053 | 1.2789 |
| Purified Water | 75.3704 | 753.7040 |  |  |  | 68.8484 |
| Physcool | 0.1000 | 1.0000 | 0.4060 | 0.2639 | 0.2932 | 0.0913 |
| Menthol | 1.0000 | 10.0000 | 4.0602 | 2.6391 | 2.9323 | 0.9135 |
| Citric Acid | 0.0270 | 0.2700 | 0.1096 | 0.0713 | 0.0792 | 0.0247 |
| Cherry Flavor (Givudan) | 0.1500 | 1.5000 | 0.6090 | 0.3959 | 0.4399 | 0.1370 |
| Peppermint Flavor | 0.5000 | 5.0000 | 2.0301 | 1.3196 | 1.4662 | 0.4567 |
| Mono ammonium glycyrrhizinate (MAG) | 0.0100 | 0.1000 | 0.0406 | 0.0264 | 0.0293 | 0.0091 |
| Polysorbate 80 NF | 0.3500 | 3.5000 | 1.4211 | 0.9237 | 1.0263 | 0.3197 |
| Atmos 300 | 0.3500 | 3.5000 | 1.4211 | 0.9237 | 1.0263 | 0.3197 |
| Glycerine | 3.0000 | 30.0000 | 12.1805 | 7.9173 | 8.7970 | 2.7404 |
| Olive Oil | 0.5000 | 5.0000 | 2.0301 | 1.3196 | 1.4662 | 0.4567 |
| FD&C green #3 | 0.0026 | 0.0260 | 0.0106 | 0.0069 | 0.0076 | 0.0024 |
| Titanium Dioxide | 0.2500 | 2.5000 | 1.0150 | 0.6598 | 0.7331 | 0.2284 |
| Total w/o active |  | 0.0000 | 100.0000 | 65.0000 |  |  |
| Total with active | 100.0000 | 1094.7292 |  | 90.0000 | 100.0000 | 100.0000 |

*assuming that all water is evaporated

The active film was very thin, blue and gritty. Sensations of bitterness and numbness were minimal, but the flavor was not entirely agreeable.

Example 4

Films of the invention having the ingredients listed in Table 4 were prepared in accordance with the method of Example 1, except that Step F comprised adding uncoated dextromethorphan hydrobromide and AMBERLITE resin to Preparation E as separate ingredients.

TABLE 4

| Material | % w/w in batch | g/batch | % w/w* placebo film | mg/dose* | % w/w* active film | % w/w actual batch |
|---|---|---|---|---|---|---|
| Dextromethorphan | | 17.0326 | | 15.0000 | 15.7563 | 5.0951 |
| Amberlite IRP69 | | 17.2597 | | 15.2000 | 15.9664 | 5.1630 |
| Xanthan Gum | 0.0600 | 0.1800 | 0.2439 | 0.1585 | 0.1665 | 0.0538 |
| Locust Bean Gum | 0.0700 | 0.2100 | 0.2845 | 0.1849 | 0.1943 | 0.0628 |
| Carrageenan | 0.3000 | 0.9000 | 1.2194 | 0.7926 | 0.8326 | 0.2692 |
| Pullulan | 16.0000 | 48.0000 | 65.0338 | 42.2720 | 44.4033 | 14.3587 |
| Potassium Sorbate | 0.0600 | 0.1800 | 0.2439 | 0.1585 | 0.1665 | 0.0538 |
| Acesulfame Potassium Salt | 0.5000 | 1.5000 | 2.0323 | 1.3210 | 1.3876 | 0.4487 |
| Aspartame NF | 1.4000 | 4.2000 | 5.6905 | 3.6988 | 3.8853 | 1.2564 |
| Purified Water | 75.3974 | 226.1922 | | | | 67.6630 |
| Physcool | 0.1000 | 0.3000 | 0.4065 | 0.2642 | 0.2775 | 0.0897 |
| Menthol | 1.0000 | 3.0000 | 4.0646 | 2.6420 | 2.7752 | 0.8974 |
| Citric Acid | 0.0000 | 0.0000 | 0.0000 | 0.0000 | 0.0000 | 0.0000 |
| Cherry Flavor (Givudan) | 0.1500 | 0.4500 | 0.6097 | 0.3963 | 0.4163 | 0.1346 |
| Peppermint Flavor | 0.5000 | 1.5000 | 2.0323 | 1.3210 | 1.3876 | 0.4487 |
| Mono ammonium glycyrrhizinate (MAG) | 0.0100 | 0.0300 | 0.0406 | 0.0264 | 0.0278 | 0.0090 |
| Polysorbate 80 NF | 0.3500 | 1.0500 | 1.4226 | 0.9247 | 0.9713 | 0.3141 |
| Atmos 300 | 0.3500 | 1.0500 | 1.4226 | 0.9247 | 0.9713 | 0.3141 |
| Glycerine | 3.0000 | 9.0000 | 12.1938 | 7.9260 | 8.3256 | 2.6923 |
| Olive Oil | 0.5000 | 1.5000 | 2.0323 | 1.3210 | 1.3876 | 0.4487 |
| FD&C green #3 | 0.0026 | 0.0078 | 0.0106 | 0.0069 | 0.0072 | 0.0023 |
| Titanium Dioxide | 0.2500 | 0.7500 | 1.0162 | 0.6605 | 0.6938 | 0.2244 |
| Total w/o active | | 300.0000 | 100.0000 | 65.0000 | | |
| Total with active | 100.0000 | 334.2922 | | 95.2000 | 100.0000 | 100.0000 |

*assuming that all water is evaporated

The active film had a pleasing appearance and taste.

Example 5

The ingredients listed in Table 5 were combined to provide an example of an antitussive film of the invention in accordance with the following procedure:

A. The water was heated to 75° C. Uncoated dextromethorphan hydrobromide was dissolved with mixing in the water, while maintaining the temperature at 75° C. AMBERLITE resin was then mixed into the water with heating for 4 to 5 hours at 70–80° C. Heating was stopped, water lost to evaporation was replaced, and the potassium sorbate and sweeteners were then added to the composition with mixing to form Preparation A.

B. The film-forming ingredients (e.g., xanthan gum, locust bean gum, carrageenan and pullulan) were mixed in a separate container to form Preparation B.

C. Preparation B was slowly added to Preparation A with rapid mixing, followed by overnight mixing at a reduced rate to provide Preparation C.

D. The menthol was dissolved with mixing in the alcohol in a separate container. The Physcool was then dissolved with mixing therein. The MAG, Polysorbate 80, Atmos 300 and flavors were then added to the mixture and mixed to enhanced uniformity to form Preparation D.

E. Preparation D, glycerine and mannitol were added to Preparation C with thorough mixing to provide Preparation E.

Preparation E was poured on a mold and cast to form a film of a desired thickness at room temperature. The film was dried under warm air and cut to a desired dimension (dictated by, e.g., dosage and mouthfeel) for taste testing. The film was segmented into 1.5 in$^2$ (9.7 cm$^2$) dosage units, each of which had a thickness of 0.009±0.002 in (0.23±0.05 mm) and a weight of 70±3 mg.

A placebo film was also prepared in accordance with the foregoing to facilitate evaluation of, e.g., the taste and appearance of the active film.

TABLE 5

| Material | % w/w in batch | g/batch | mg/dose* | % w/w* film | % w/w actual batch |
|---|---|---|---|---|---|
| Dextromethorphan HBr | | 11.4615 | 15.0000 | 21.4286 | 9.2666 |
| Amberlite IRP69 | | 12.2256 | 16.0000 | 22.8571 | 9.8843 |
| Xanthan Gum | 0.0600 | 0.0600 | 0.0944 | 0.1348 | 0.0485 |
| Locust Bean Gum | 0.0700 | 0.0700 | 0.1101 | 0.1573 | 0.0566 |
| Carrageenan | 0.3000 | 0.3000 | 0.4718 | 0.6740 | 0.2425 |
| Pullulan | 16.0000 | 16.0000 | 25.1613 | 35.9447 | 12.9359 |
| Potassium Sorbate | 0.0600 | 0.0600 | 0.0944 | 0.1348 | 0.0485 |
| Acesulfame Potassium Salt | 0.5000 | 0.5000 | 0.7863 | 1.1233 | 0.4042 |
| Aspartame NF | 1.4000 | 1.4000 | 2.2016 | 3.1452 | 1.1319 |
| Purified Water | 70.2000 | 70.2000 | | | 56.7561 |
| Alcohol USP | 5.0000 | 5.0000 | | | 4.0425 |
| Physcool | 0.1000 | 0.1000 | 0.1573 | 0.2247 | 0.0808 |
| Menthol | 1.5000 | 1.5000 | 2.3589 | 3.3698 | 1.2127 |
| Peppermint Flavor | 0.1000 | 0.1000 | 0.1573 | 0.2247 | 0.0808 |
| Raspberry Flavor (Givudan) | 0.5000 | 0.5000 | 0.7863 | 1.1233 | 0.4042 |
| Mono ammonium glycyrrhizinate (MAG) | 0.0100 | 0.0100 | 0.0157 | 0.0225 | 0.0081 |
| Polysorbate 80 NF | 0.3500 | 0.3500 | 0.5504 | 0.7863 | 0.2830 |
| Atmos 300 | 0.3500 | 0.3500 | 0.5504 | 0.7863 | 0.2830 |
| Glycerine | 1.5000 | 1.5000 | 2.3589 | 3.3698 | 1.2127 |
| Mannitol USP | 2.0000 | 2.0000 | 3.1452 | 4.4931 | 1.6170 |
| Total w/o active | | 100.0000 | 39.0000 | | |

The active film had a pleasing appearance and taste.

Example 6

Films of the invention having the ingredients listed in Table 6 were prepared in accordance with the method of Example 5.

TABLE 6

| Material | % w/w in batch | g/batch | mg/dose* | % w/w* | % w/w |
|---|---|---|---|---|---|
| Dextromethorphan HBr | | 11.6538 | 15.0000 | 21.4286 | 9.3919 |
| Amberlite IRP69 | | 12.4308 | 16.0000 | 22.8571 | 10.0180 |
| Xanthan Gum | 0.0600 | 0.0600 | 0.0925 | 0.1321 | 0.0484 |
| Locust Bean Gum | 0.0700 | 0.0700 | 0.1079 | 0.1542 | 0.0564 |
| Carrageenan | 0.3000 | 0.3000 | 0.4625 | 0.6606 | 0.2418 |
| Pullulan | 16.0000 | 16.0000 | 24.6640 | 35.2343 | 12.8944 |
| Potassium Sorbate | 0.0600 | 0.0600 | 0.0925 | 0.1321 | 0.0484 |
| Acesulfame Potassium Salt | 0.5000 | 0.5000 | 0.7708 | 1.1011 | 0.4030 |
| Aspartame NF | 1.4000 | 1.4000 | 2.1581 | 3.0830 | 1.1283 |
| Purified Water | 69.7000 | 69.7000 | | | 56.1713 |
| Alcohol USP | 5.0000 | 5.0000 | | | 4.0295 |
| Physcool | 0.1000 | 0.1000 | 0.1542 | 0.2202 | 0.0806 |
| Menthol | 2.0000 | 2.0000 | 3.0830 | 4.4043 | 1.6118 |
| Peppermint Flavor | 0.1000 | 0.1000 | 0.1542 | 0.2202 | 0.0806 |
| Raspberry Flavor (Givudan) | 0.5000 | 0.5000 | 0.7708 | 1.1011 | 0.4030 |
| Mono ammonium glycyrrhizinate (MAG) | 0.0100 | 0.0100 | 0.0154 | 0.0220 | 0.0081 |
| Polysorbate 80 NF | 0.3500 | 0.3500 | 0.5395 | 0.7708 | 0.2821 |
| Atmos 300 | 0.3500 | 0.3500 | 0.5395 | 0.7708 | 0.2821 |
| Glycerine | 1.5000 | 1.5000 | 2.3123 | 3.3032 | 1.2089 |
| Mannitol USP | 2.0000 | 2.0000 | 3.0830 | 4.4043 | 1.6118 |
| Total w/o active | | 0.0000 | 39.0000 | | |
| Total with active | 100.0000 | 124.0846 | 70.0000 | 100.0000 | 100.0000 |

*assuming that all water and alcohol is evaporated

The active film had a pleasing appearance and taste.

Example 7

A film of the invention having the ingredients listed in Table 7 were prepared in accordance with the method of Example 5. The film was segmented into 1"×1.25" (2.54 cm×3.18 cm) dosage units, each of which had a thickness of 0.009±0.002 in (0.23±0.05 mm) and a weight of 63.6±3 mg.

TABLE 7

| Material | % w/w in batch | kg/batch | mg/dose* | % w/w* | % w/w |
|---|---|---|---|---|---|
| Dextromethorphan HBr | | 1.3567 | 15.0000 | 23.5981 | 9.3918 |
| Amberlite IRP69 | | 1.4472 | 16.0000 | 25.1713 | 10.0180 |
| Xanthan Gum | 0.0600 | 0.0070 | 0.0772 | 0.1215 | 0.0484 |
| Locust Bean Gum | 0.0700 | 0.0081 | 0.0901 | 0.1417 | 0.0564 |
| Carrageenan | 0.3000 | 0.0349 | 0.3661 | 0.6075 | 0.2418 |
| Pullulan | 16.0000 | 1.8627 | 20.5941 | 32.3988 | 12.8944 |
| Potassium Sorbate | 0.0600 | 0.0070 | 0.0772 | 0.1215 | 0.0484 |
| Acesulfame Potassium Salt | 0.5000 | 0.0582 | 0.6436 | 1.0125 | 0.4030 |
| Aspartame NF | 1.4000 | 0.1630 | 1.8020 | 2.8349 | 1.1283 |
| Purified Water | 69.7000 | 8.1145 | | | 56.1714 |
| Alcohol USP | 5.0000 | 0.5821 | | | 4.0295 |
| Physcool | 0.1000 | 0.0116 | 0.1287 | 0.2025 | 0.0806 |
| Menthol | 2.0000 | 0.2328 | 2.5743 | 4.0498 | 1.6118 |
| Peppermint Flavor | 0.1000 | 0.0116 | 0.1287 | 0.2025 | 0.0806 |
| Raspberry Flavor (Givudan) | 0.5000 | 0.0582 | 0.6436 | 1.0125 | 0.4030 |
| Mono ammonium glycyrrhizinate (MAG) | 0.0100 | 0.0012 | 0.0129 | 0.0202 | 0.0081 |
| Polysorbate 80 NF | 0.3500 | 0.0407 | 0.4505 | 0.7087 | 0.2821 |
| Atmos 300 | 0.3500 | 0.0407 | 0.4505 | 0.7087 | 0.2821 |
| Glycerine | 1.5000 | 0.1746 | 1.9307 | 3.0374 | 1.2089 |
| Mannitol USP | 2.0000 | 0.2328 | 2.5743 | 4.0498 | 1.6118 |
| Total w/o active + resin | | 11.6420 | 32.5644 | | |
| Total with active + resin | 100.0000 | 14.4459 | 63.5644 | 100.0000 | 100.0000 |

*assuming that all water and alcohol is evaporated

The active film had a pleasing appearance and taste.

While the invention has been described in detail and with reference to specific examples thereof, it will be apparent to one skilled in the art that various changes and modifications can be made therein without departing from the spirit and scope thereof.

What is claimed is:

1. An orally consumable solid film comprising:
   at least one water soluble polymer, and
   an adsorption complex, said adsorption complex comprising at least one pharmaceutically active agent and at least one ion exchange resin as a taste masking agent; and
   wherein the ratio of the at least one pharmaceutically active agent to the at least one ion exchange resin is about 1:3 to about 3:1; and wherein said orally consumable film is adapted to adhere to and dissolve in a mouth of a consumer.

2. The consumable solid film according to claim 1, wherein said water soluble polymer is selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

3. The consumable solid film according to claim 2, wherein said water soluble polymer is pullulan.

4. The consumable solid film according to claim 1, wherein said pharmaceutically active agent is selected from the group consisting of antimicrobial agents, non-steroidal anti-inflammatory agents, antitussives, decongestants, antihistamines, expectorants, anti-diaherrals, $H_2$-antagonists, proton pump inhibitors, central nervous system agents, analgesics and mixtures thereof.

5. The consumable solid film according to claim 1 wherein the pharmaceutically active agent provides from about 40 wt % to about 60 wt % of said adsorption complex.

6. The consumable solid film according to claim 5, wherein the ion exchange resin is a sulfonated polymer comprising polystyrene cross-linked with divinylbenzene.

7. The consumable solid film according to claim 5, wherein the ion exchange resin is a sulfonated polymer comprising polystyrene cross-linked with 8% of divinylbenzene, with an ion exchange capacity of about 4.5 to 5.5 meq/g of dry resin (H$^+$-form).

8. The consumable solid film according to claim 7, wherein the ion exchange resin comprises irregularly-shaped particles ranging in size from about 47 to about 149 micrometers.

9. The consumable solid film according to claim 7, wherein the ion exchange resin comprises spherical particles ranging in size from about 45 to about 150 micrometers.

10. The consumable solid film according to claim 5, wherein the ion exchange resin comprises polystyrene cross-linked with 8% of divinylbenzene functionalized with a quaternary ammonium group, said ion exchange resin having an exchange capacity normally within a range of about 3 to about 4 meq/g of dry ion exchange resin.

11. The consumable solid film according to claim 5, wherein said water soluble polymer is pullulan, said pharmaceutically active agent is dextromethorphan, and said taste masking agent is a sulfonated polymer ion exchange resin comprising polystyrene cross-linked with divinylbenzene.

12. The consumable solid film according to claim 11, comprising pullulan in an amount of about 40 to about 80 wt % of said film, dextromethorphan in an amount of about 5 to about 40 wt % of said film, and sulfonated polymer ion exchange resin in an amount of about 5 to about 40 wt % of said film.

13. A method for preparing the consumable solid film of claim 1, said method comprising:
   dissolving the water-soluble polymer in water to provide an aqueous solution;
   mixing water soluble film former and stabilizing agent to provide a solid-film forming mixture;
   combining said solid-film forming mixture and said aqueous solution to provide a hydrated polymer gel;
   mixing oils to form an oil mixture;
   admixing said oil mixture and said hydrated polymer gel to provide a uniform gel, said uniform gel comprising said pharmaceutically active agent and said at least one ion exchange resin;
   casting the uniform gel on a substrate; and
   drying the cast gel to provide said solid film.

14. The method of claim 13, wherein said aqueous solution comprises both said pharmaceutically active agent and said at least one ion exchange resin.

15. The method of claim 13, wherein said pharmaceutically active agent is sorbed to said ion exchange resin without separating ion exchanged pharmaceutically active agent from unexchanged agent and counter ion salts.

16. An orally consumable solid film comprising a water soluble polymer, a pharmaceutically active agent and an ion exchange resin taste masking agent wherein said ion exchange resin is present at a weight ratio to said pharmaceutically active agent of about 2:1 to about 1:2 and said orally consumable film is adapted to adhere to and dissolve in a mouth of a consumer.

17. The consumable solid film according to claim 16, wherein the ratio of ion exchange resin to pharmaceutically active agent is about 1:1.

18. The consumable film according to claim 12, wherein pullulan is present in said solid film in an amount of about 2 to about 6 mg/cm$^2$, dextromethorphan is present in said solid film in an amount of about 1.4 to about 2 mg/cm$^2$, and sulfonated polymer ion exchange resin is present in said solid film in an amount of about 1.4 to about 2 mg/cm$^2$.

19. The consumable solid film according to claim 12 or 18, further comprising:
   about 0.01 to about 5 w % of at least one stabilizing agent;
   about 0.001 to about 0.1 wt % of at least one of at least one coloring agent;
   about 0.01 to about 70 wt % water;
   about 0.1 to about 15 wt % of at least one sweetening agent;
   about 0.1 to about 15 w % of at least one flavoring agent;
   about 0.1 to about 4 wt % of at least one cooling agent;
   about 0.1 to about 5 wt % of at least one surfactant;
   about 0.1 to about 12 wt % of a triglyceride;
   about 0.001 to about 5 wt % of a preservative;
   about 0.01 to about 5 wt/o of a polyethylene oxide compound; and
   about 1 to about 20 wt % of propylene glycol.

20. The consumable solid film according to claim 1 wherein the pharmaceutically active agent comprises dextromethorphan or salt thereof or both.

21. The consumable solid film according to claim 1 wherein the pharmaceutically-active agent comprises phenylepherine or salt thereof or both.

22. The consumable solid film according to claim 2 wherein said water soluble polymer comprises polyvinyl alcohol.

23. The consumable solid film according to claim 2 wherein said water soluble polymer comprises hydroxypropyl cellulose.

24. The consumable solid film according to claim 1 wherein the pharmaceutically active agent comprises diphenhydramine or salt thereof or both.

25. The consumable solid film according to claim 2, wherein said pharmaceutically active agent is selected from the group consisting of antimicrobial agents, non-steroidal anti-inflammatory agents, antitussives, decongestants, anti-histamines, expectorants, anti-diaherrals, H$_2$-antagonists, proton pump inhibitors, central nervous system agents, analgesics and mixtures thereof.

26. The consumable solid film according to claim 1, wherein said film has a thickness of 0.009±0.002 in.

27. The consumable solid film according to claim 1, wherein said film contains about 0.1% to about 10 wt % moisture.

28. The consumable solid film according to claim 1, wherein said film contains about 3% to about 8 wt % moisture.

29. The consumable solid film according to claim 1, wherein said film contains about 4% to about 7 wt % moisture.

30. An orally consumable solid film comprising:
   at least one water soluble polymer selected from the group consisting of pullulan, hydroxypropylmethyl cellulose, and hydroxypropyl cellulose, and mixtures thereof; and
   an adsorption complex, said adsorption complex comprising at least one pharmaceutically active agent and at least one ion exchange resin as a taste masking agent;
   wherein said pharmaceutically active agent is selected from the group consisting of antimicrobial agents, non-steroidal anti-inflammatory agents, antitussives, decongestants, anti-histamines, expectorants, anti-diaherrals, H$_2$-antagonists, proton pump inhibitors, central nervous system agents, analgesics and mixtures thereof; and wherein the ratio of the at least one pharmaceutically active agent to the at least one ion exchange resin is about 1:3 to about 3:1; and wherein said orally consumable film is adapted to adhere to and dissolve in a mouth of a consumer.

31. The consumable solid film according to claim 30 wherein the pharmaceutically active agent comprises dextromethorphan or salt thereof or both.

32. The consumable solid film according to claim 30 wherein the pharmaceutically-active agent comprises phenylepherine or salt thereof or both.

33. The consumable solid film according to claim 30 wherein the pharmaceutically active agent comprises diphenhydramine or salt thereof or both.

* * * * *